(12) United States Patent
Marder

(10) Patent No.: US 9,205,093 B2
(45) Date of Patent: Dec. 8, 2015

(54) HYDROCORTISONE NANOTECHNOLOGICAL DELIVERY SYSTEM

(76) Inventor: Gary Marder, Port St. Lucie, FL (US)

( * ) Notice: Subject to any disclaimer, the term of this patent is extended or adjusted under 35 U.S.C. 154(b) by 127 days.

(21) Appl. No.: 13/610,138

(22) Filed: Sep. 11, 2012

(65) Prior Publication Data

US 2014/0073616 A1 Mar. 13, 2014

(51) Int. Cl.
| | |
|---|---|
| A61K 31/56 | (2006.01) |
| A61K 31/075 | (2006.01) |
| A61K 31/05 | (2006.01) |
| A61K 31/573 | (2006.01) |
| A61K 9/00 | (2006.01) |
| A61K 47/24 | (2006.01) |
| A61K 47/32 | (2006.01) |
| A61K 9/14 | (2006.01) |
| B82Y 5/00 | (2011.01) |

(52) U.S. Cl.
CPC ............ *A61K 31/573* (2013.01); *A61K 9/0014* (2013.01); *A61K 9/14* (2013.01); *A61K 31/05* (2013.01); *A61K 47/24* (2013.01); *A61K 47/32* (2013.01); *B82Y 5/00* (2013.01)

(58) Field of Classification Search
USPC ........... 552/502; 514/181, 179, 720, 733, 881
See application file for complete search history.

(56) References Cited

U.S. PATENT DOCUMENTS

| | | | | | |
|---|---|---|---|---|---|
| 4,722,837 | A | * | 2/1988 | Cameron ................ | A61K 8/23 424/705 |
| 4,835,148 | A | * | 5/1989 | Barford ................. | A61K 8/463 514/179 |
| 5,436,010 | A | * | 7/1995 | Lau ....................... | A61K 8/14 424/450 |
| 5,653,989 | A | * | 8/1997 | Sattler .................. | A61K 9/0014 424/401 |
| 2003/0228269 | A1 | * | 12/2003 | DeRosa ................. | A61Q 5/006 424/70.1 |
| 2008/0234159 | A1 | * | 9/2008 | Anantaneni ........... | A61K 8/466 510/129 |
| 2010/0297199 | A1 | * | 11/2010 | Duan et al. ............ | 424/401 |
| 2011/0129546 | A1 | * | 6/2011 | Umbert Mill ......... | 424/639 |

FOREIGN PATENT DOCUMENTS

| | | | |
|---|---|---|---|
| WO | WO 9409763 A1 * | 5/1994 | |
| WO | WO9904747 A2 * | 2/1999 | ............... A61K 7/00 |
| WO | WO 2009074239 A1 * | 6/2009 | |

OTHER PUBLICATIONS

Bentley, M.V.L.B., et al. International Journal of Pharmaceutics vol. 146. pp. 255-262. Published 1997.*
Fini, A., et al. AAPS PharmSciTech vol. 9, pp. 762-768. Pulished 2008.*
ISELUX product page. Published 2010.*
Bentley, M.V.L.B., et al., International Journal of Pharmaceutics vol. 146, pp. 255-262. Published 1997.*
Cocamide MEA product page. (Kao Chemicals Europe, published 1994).*

* cited by examiner

*Primary Examiner* — Paul Zarek
*Assistant Examiner* — George W Kosturko
(74) *Attorney, Agent, or Firm* — Laurence Greenberg; Werner Stemer; Ralph Locher

(57) ABSTRACT

A composition is provided having nano technological delivery of a medicament through the skin. The composition contains hydrocortisone, resveratrol and a sulfate free surfactant. The composition is formulated into a shampoo and the shampoo facilitates nano technological delivery of the hydrocortisone and the resveratrol through the skin of a user.

7 Claims, No Drawings

HYDROCORTISONE NANOTECHNOLOGICAL DELIVERY SYSTEM

BACKGROUND OF THE INVENTION

Field of the Invention

The skin surface of mammals is constructed to repel most molecules. The skin acts as a barrier to protect the interior of a mammal. Topical applications have been developed whereby various molecules are absorbed through the skin. In addition to topical applications, transdermal drug delivery has become an increasingly popular method for, among other reasons, high levels of patient compliance. There still exists a difficulty in transport of molecules through the various epidermal membranes in order to effectuate drug absorption through the skin. One method is to provide a carrier that assists in the transport of micron, sub-micron and nano sized particles through the layers of the epidermis. Safe and reproducible drug delivery can be achieved with deformable and stable nano-sized carriers. The nano-sized carriers encompass materials that to some degree deform the various pores in the skin allowing for the transport of materials through and contrary to the skins natural barrier configuration.

Although hydrocortisone products are known for topical use, they typically are not used in shampoo formulations.

SUMMARY OF THE INVENTION

The present invention encompasses a composition, a method of manufacture and a method of application of a nanotechnological delivery of hydrocortisone and resveratrol in a topical preparation.

In one embodiment, the invention is a composition for the nano technological delivery of a medicament in a shampoo base. The main component is hydrocortisone. Hydrocortisone, as used herein, includes the organic freebase, salts, isomers, and racemates. In one embodiment hydrocortisone acetate is used. In one embodiment, the composition contains hydrocortisone, resveratrol, and a surfactant. In one embodiment, the composition contains hydrocortisone, and a sulfate free surfactant. The composition is formulated into a shampoo and the shampoo facilitates nano technological delivery of the hydrocortisone, resveratrol, lecithin, and glycerin through the skin of a user.

The hydrocortisone is present in amounts of about 0.01 to 1.00 percent w/w and resveratrol is present in a resveratrol composition wherein the composition is 1% w/w resveratrol in a carrier base of glycerin and lecithin in an amount of approximately 0.01 to 1.00 percent w/w. As used herein, the term "resveratrol composition" refers to a composition containing 1% resveratrol in a carrier of lecithin and glycerin. There is 0.01-1.00 percent w/w of the resveratrol composition in the total formulation.

In one embodiment, the resveratrol composition of 1.00% resveratrol w/w is in a carrier base consisting of lecithin and glycerin.

Additionally, the composition of the present invention is formulated into a topical preparation as desired. The topical preparation includes, but is not limited to the aforementioned shampoo, cream, ointment, gel, lotion, and any other liquid, solution, suspension, mixture, emulsion, semi-solid or the like.

One preferred surfactant is sodium lauroyl methyl isethionate and the composition is formulated to contain approximately 10 to 30 percent w/w.

The present invention has discovered that through a unique ratio of hydrocortisone and resveratrol composition, the efficacy is enhanced. Efficacy being defined as the absorption into the skin. In one embodiment the hydrocortisone and resveratrol composition is present in a ratio of about 1:1-1:2.

In another embodiment, the hydrocortisone and the resveratrol composition are present in a ratio of about 1:0.1-1:2.

In another embodiment, the hydrocortisone and the resveratrol composition are present in a ratio of about 0.1:1-0.1:2.

Also contemplated is a method of delivering an active component through the skin of a mammal. The method utilizes a nanotechnological delivery system containing the steps of: providing a composition according to the present invention; applying the composition to the skin of a mammal; and absorbing the composition. The absorbing includes leaving the composition on the skin. Water is used to rinse the composition from the skin of the mammal. In a preferred embodiment, the method encompasses providing the composition formulated and presented to a user as a shampoo. The shampoo is applied to the scalp, allowed to remain, and rinsed.

The absorbing includes leaving the composition in place after the applying step for a period of time from 5-300 seconds.

This method is further applicable to all skin surfaces and equally applicable when the topical composition formulated with nanotechnological delivery system of the present invention is formulated and presented as cream, ointment, gel, lotion, foam, paste, and any other liquid mixture such as aqueous mixture and/or aqueous-organic mixture, solution, suspension, mixture, emulsion, semi-solid and the like.

DETAILED DESCRIPTION OF THE PREFERRED EMBODIMENT

The invention encompasses a transdermal delivery of a combined composition containing hydrocortisone and a resveratrol composition. Each of the hydrocortisone and resveratrol composition is formulated utilizing particular ratios that have been shown to have an advantageous synergistic effect in effectuating trans-dermal drug delivery. In a preferred embodiment, the present invention encompasses formulation of hydrocortisone and resveratrol in a shampoo composition. The composition includes a plurality of components to enhance the nanotechnological delivery of the active components through the skin.

In one embodiment, the shampoo has a formulation as in Table 1 below.

TABLE 1

| Component | % w/w |
| --- | --- |
| Water | 20.0-50.0 |
| Acrylates Crosspolymer-4 | 0.1-10.0 |
| Panthenol | 0.00001-0.1 |
| Caffeine | 0.00001-0.1 |
| Tetrasodium EDTA | 0.01-0.5 |
| Glycol Distearate (and) Cocamide DEA (and) CocamidopropylBetaine (and) Glycerin | 0.01-1.0 |
| Glycol Stearate | 0.1-10.0 |
| Cocamide MEA | 0.1-10.0 |
| Glycol Distearate | 0.1-10.0 |
| Sodium Lauroyl Methyl Isethionate | 0.1-10.0 |
| Cholecalciferol (and) *Zea Mays* (Corn) Oil | 0.00001-0.1 |
| Sodium Lauroyl Sarcocinate | 10.0-30.0 |
| Sodium C14-16 Olefin Sulfonate | 0.1-10.0 |
| Potassium Cocoate | 0.1-10.0 |

TABLE 1-continued

| Component | % w/w |
|---|---|
| CocamidopropylBetaine | 5.0-20.0 |
| Polyquaternium-39 | 0.1-10.0 |
| DMDM Hydantoin | 0.1-1.0 |
| Methylchloroisothiazolinone (and) Methylisothiazolinone | 0.00001-0.09 |
| Propylene Glycol | 0.1-10.0 |
| Camellia Sinensis Leaf Extract (and) Water (and) Glycerin | 0.00001-0.1 |
| Tocopheryl Acetate | 0.00001-0.1 |
| Magnesium Ascorbyl Phosphate | 0.00001-0.1 |
| RetinylPalmitate | 0.00001-0.1 |
| Methyldihydrojasmonate (and) Amyl Salicylate (and) Isobutyl Methyl Tetrahydropyranol (and) Ethylene Brassylate (and) 2,-Dimethyl-7-Octen-2-OL (and) Linalool (and) TetramethylAcetyloctahydronaphthalenes (and) Phenethyl Alcohol (and) Oxacyclohexadecenone (and) MethylenedioxyphenylMethylpropanal (and) CoriandrumSativum (Coriander) Fruit Oil (and) Isopropylphenylbutanal (and) Decanal | 0.1-2.0 |
| PPG-5 Ceteth-20 | 0.1-2.0 |
| Styrene/Acrylates Copolymer | 0.01-1.0 |
| Citric Acid [50%] (and) Water [50%] | 0.01-1.0 |
| Sodium Chloride | 0.01-1.0 |
| With active components of | |
| Hydrocortisone | 0.01-1.00 |
| Resveratrol Composition | 0.01-1.00. |

In a preferred embodiment, when formulated as a shampoo, a base is prepared starting with acrylate crosspolymer-4 in water. Although many materials are suitable and known for shampoo formulation in general and particularly for a formulation with a desired viscosity, the selected acrylate crosspolymer-4 is selected based on the characteristics of imparting a desired viscosity and compatibly with the nanotechnology delivery components. This particular component in the above-stated range is particular for compatibility for both the active materials of hydrocortisone and resveratrol.

A preferred acrylate crosspolymer-4 is Carbopol aqua SF-2 polymer (available from Lubrizol, Wickcliffe, Ohio). Additionally, the initial base is prepared with panthenol, caffeine and tetrasodium EDTA. Once the initial base is prepared and a solution is obtained, various components selected with particularity and criticality as to percentage composition and chemistry are added to the base.

The next step includes adding glycol distearate, cocamide DEA, and cocamidoproplbetaine with glycerin. Additionally, glycol stearate, cocamide MEA, glycol distearate, sodium lauroyl methyl Isethionate, cholecalciferol and zea mays are added to the base.

Although it is well known in the art that there are numerous surfactant bases suitable for shampoos in general and medical shampoos in particular, it has been discovered in formulas of the present invention that in order to deliver hydrocortisone and resveratrol utilizing a nano technology delivery system a sulfate free surfactant needs to be utilized. In a preferred embodiment the surfactant of the present invention incorporates approximately 10 to 30 percent of sodium lauroyl sarcocinate. A preferred material is available from RITA Corporation and sold as RitaFactant LS-30. This material is selected with particularity as to composition and to percentage used in the formulation of the present invention in order to provide improved delivery of the active in a nanotechnology delivery system.

In a preferred embodiment micronized hydrocortisone is utilized. Hydrocortisone is present in a range of 0.1 to 1.0 percent w/w. The particular micronization properties require a preferred material that has a particle size of not less than 90 percent of the particles less than or equal to five microns. Although, as stated herein, 90% is less than 5 microns, it is generally understood in the art that particle size measurements are typically measured and presented as a Gaussian curve with the major portion of the curve demonstrating particle size between about 1 to 5 microns.

In a preferred embodiment, the shampoo is produced in a method as now described.

Step 1
Add ingredients
Water,
Acrylates Crosspolymer-4,
Panthenol,
Caffeine, and
Tetrasodium EDTA—in order in a suitable main kettle and mixed under propeller agitation.
Start heating ingredients to 78° C.-80° C.

Step 2
Once desired temperature is reached, add the following while maintaining temperature and mixing.
Glycol Distearate,
Cocamide DEA,
CocamidopropylBetaine,
Glycerin,
Glycol Stearate,
Cocamide MEA,
Glycol Distearate,
Sodium Lauroyl Methyl Isethionate,
Cholecalciferol, and
Zea Mays (Corn) Oil.

Step 3
Once Steps 1-2 are at 78° C.-80° C., add, in order:
Sodium Lauroyl Sarcocinate,
Sodium C14-16 Olefin Sulfonate, and
Potassium Cocoate.
Continue to mix until all ingredients are dissolved and maintain temperature at 78° C.-80° C.

Step 4
When a uniform mixture is achieved, cool the batch to 70° C.-75° C. When the batch is 70°-75° C., add:
CocamidopropylBetaine—under propeller agitation and mix until uniform.

Step 5
When a uniform mixture is achieved, cool the mixture to 45° C.-50° C.
Then add, while mixing—Polyquaternium-39.
Mix until uniform.

Step 6
When a uniform mixture is achieved, cool the mixture 40° C. and add:
DMDM Hydantoin,
Methylchloroisothiazolinone, and
Methyl isothiazolinone.
Added in order under propeller agitation. Mix until uniform.

Step 7
In a second, or auxiliary vessel, premix the following ingredients in advance under homogenizer agitation and mix until thoroughly dispersed:
Propylene Glycol,
Hydrocortisone,
Reservatrol,
Glycerin, and
Lecithin.

Add the mixture from the second vessel to the main vessel (Steps 1-6) where the main vessel is at 40° C. The adding of the secondary vessel components are added to the main vessel under propeller agitation.

Step 8

When the mixture of step 7 is uniform, cool the batch to 35° C. and add:
Camellia Sinensis Leaf Extract (and) Water (and) Glycerin,
Tocopheryl Acetate,
Magnesium Ascorbyl Phosphate,
RetinylPalmitate, and
Cholecalciferol (and) *Zea Mays* (Corn) Oil.

The materials in step 8 are added under propeller agitation.

Step 9

In a third vessel, premix ingredients under propeller agitation and mix until clear and uniform. The phase can optionally be warmed to 40° C. while mixing:
Methyldihydrojasmonate,
Amyl Salicylate,
Isobutyl Methyl Tetrahydropyranol,
Ethylene Brassylate,
2,-Dimethyl-7-Octen-2-OL,
Linalool,
TetramethylAcetyloctahydronaphthalenes,
Phenethyl Alcohol,
Oxacyclohexadecenone,
MethylenedioxyphenylMethylpropanal,
CoriandrumSativum (Coriander) Fruit Oil Isopropylphenylbutanal,
Decanal,
PPG-5 Ceteth-20, and
Styrene/Acrylates Copolymer.

Step 10

When the main product batch (Steps 1-8) is at 35° C., add premixed step 9 mixture to main product batch under propeller agitation. Mix until uniform.

Step 11

When the batch is uniform, add styrene/Acrylates Copolymer and mix until uniform.

Step 12

When the batch is uniform, take the pH of the batch and use (Citric Acid 50% Solution) to adjust the pH to 5.50-6.00.

Step 13

After the pH has been adjusted, take the viscosity of the batch. Vicosity can be measured in any acceptable manner including Dynamic and Kinematic measurements. A preferred measurement is using Brookfield RVT; Spindle: 4; Speed: 20 rpm; Time: 1 Minute).

A NaCl solution is used as needed to adjust the viscosity to 3,500-5,000 cps. Each of pH and viscosity are measured between 25° C. to 30° C. Care is taken, as it is known in the art that viscosity of surfactant-based compositions is correlated to a salt concentration gradient.

Step 14

When the viscosity is either in the desired range or has been adjusted into the desired range, the composition is cooled to 30° C. and discharge into suitable storage containers.

In one embodiment, the finished product exhibits the following characteristics:

Viscosity, initial
Brookfield RVT; Spindle: 4; Speed: 20 RPM; Time: 1 Minute
3,500-5,000 cps
Viscosity, 24 hr
Brookfield RVT; Spindle: 4; Speed: 20 RPM; Time: 1 Minute
4,000-6,000 cps
Specific Gravity
Pycnometer
1.020 +/− 0.02
pH
5.50-6.50
24 hr Stability @ 45° C.
Observation
Stable - No separation
Microbiology Test 1
Total Aerobic Microbial Count
<=100 ufc/g
Microbiology Test 2
Salmonella, *Escherichia Coli*, *Pseudomonas Aruginosa*, *Staphylococcus Aureus*
None The present invention has discovered the enhanced nanotechnological delivery of a hydrocortisone-resveratrol composition based on the discovered base formulation and synergistic ratio of hydrocortisone:resveratrol composition. The result will provide enhanced absorption therapy over known compositions.

In one embodiment, the nanotechnolgical delivery system of the present invention is prepared as any of a cream, lotion, ointment, or gel. The cream will utilize the advantageous novel ratio of hydrocortisone, resveratrol, lecithin, and glycerin to deliver the actives in the novel nanotechnological delivery system discovered and disclosed herein.

In one embodiment, it has further been discovered that hydrocortisone formulated according to the present invention, while omitting resveratrol maintains an acceptable level of efficacy for delivery though the skin.

While the invention has been described in its preferred form or embodiment with some degree of particularity, it is understood that this description has been given only by way of example and that numerous changes in the details of construction, fabrication, and use, including the combination and arrangement of parts, may be made without departing from the spirit and scope of the invention.

I claim:

1. A shampoo composition comprising:
   hydrocortisone;
   a resveratrol composition of 1.00% resveratrol w/w in a carrier base containing lecithin and glycerin, wherein said resveratrol composition is present in an amount of 0.01 to 1.00 percent w/w based on the total weight of said shampoo composition; and sodium lauroyl methyl isethionate.

2. The composition according to claim 1, wherein said hydrocortisone is present in amount of about 0.01 to 1.00 percent w/w.

3. The composition according to claim 1, wherein the sodium lauroyl methyl isethionate is present in an amount of 10 to 30 percent w/w.

4. The composition according to claim 1, wherein said hydrocortisone and said resveratrol composition are present in a ratio in a range of 1:1-1:2.

5. The composition according to claim 1, wherein said hydrocortisone and said resveratrol composition are present in a ratio in a range of 1:0.1-1:2.

6. The composition according to claim 1, wherein said hydrocortisone and said resveratrol composition are present in a ratio in a range of 0.1:1-0.1:2.

7. The composition according to claim 1, wherein said hydrocortisone is hydrocortisone acetate.

* * * * *